(12) United States Patent
Wu et al.

(10) Patent No.: US 11,459,354 B2
(45) Date of Patent: Oct. 4, 2022

(54) PROCESS FOR PURIFYING LIRAGLUTIDE (71) Applicant: SCINOPHARM TAIWAN, LTD., Tainan (TW)

(72) Inventors: Ming-Chih Wu, Tainan (TW); Hsin-Che Huang, Tainan (TW); Tsung-Yu Hsiao, Tainan (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 169 days.

(21) Appl. No.: 16/829,725

(22) Filed: Mar. 25, 2020

(65) Prior Publication Data
US 2020/0308218 A1    Oct. 1, 2020

Related U.S. Application Data (60) Provisional application No. 62/823,147, filed on Mar. 25, 2019.

(51) Int. Cl.
*C07K 1/20* (2006.01)
*C07K 14/605* (2006.01)

(52) U.S. Cl.
CPC .............. *C07K 1/20* (2013.01); *C07K 14/605* (2013.01)

(58) Field of Classification Search
CPC ................................ C07K 1/20; C07K 14/605
See application file for complete search history.

(56) References Cited

U.S. PATENT DOCUMENTS

| 9,422,330 B2 | 8/2016 | Wu et al. | |
|---|---|---|---|
| 2015/0051372 A1 | 2/2015 | Qin et al. | |
| 2016/0015064 A1* | 1/2016 | Luo | A23L 27/88 426/2 |
| 2017/0283478 A1* | 10/2017 | Gandavadi | C07K 14/605 |

FOREIGN PATENT DOCUMENTS

| CN | 102584982 A | 7/2012 |
|---|---|---|
| CN | 102875665 A | 1/2013 |
| CN | 108794618 A | 11/2018 |
| EP | 2813514 | 12/2014 |
| WO | WO-2007/147816 | 12/2007 |
| WO | WO-2016/005960 | 1/2016 |
| WO | WO-2016/067271 | 5/2016 |
| WO | WO-2017/162653 | 9/2017 |

OTHER PUBLICATIONS

International Search Report and Written Opinion for International PCT Application No. PCT/SG2020/050156 dated Jun. 30, 2020 (11 pages).

* cited by examiner

*Primary Examiner* — Jeanette M Lieb
(74) *Attorney, Agent, or Firm* — Mintz, Levin, Cohn, Ferris, Glovsky and Popeo, P.C.

(57) ABSTRACT

The present invention provides improved processes for purifying liraglutide. Liraglutide is purified via two sequential RP-HPLC purifications followed by a salt-exchange step, where a pH is kept constant in the first and second purification steps. In particular, the processes utilize a halogenated solvent in a sample preparation step, which provides better solubility and an environment suitable for decarboxylation for crude liraglutide prior to a RP-HPLC purification.

23 Claims, 2 Drawing Sheets

Specification includes a Sequence Listing.

SEQUENCE LISTING

```
<160> NUMBER OF SEQ ID NOS: 1

<210> SEQ ID NO 1
<211> LENGTH: 31
<212> TYPE: PRT
<213> ORGANISM: Artificial sequence
<220> FEATURE:
<223> OTHER INFORMATION: Synthetic construct

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

PROCESS FOR PURIFYING LIRAGLUTIDE

CROSS-REFERENCES TO RELATED APPLICATIONS

This application claims priority to U.S. Provisional Application No. 62/823,147 filed Mar. 25, 2019, which is incorporated herein in its entirety for all purpose.

REFERENCE TO A "SEQUENCE LISTING," A TABLE, OR A COMPUTER PROGRAM LISTING APPENDIX SUBMITTED ON A COMPACT DISK

The Sequence Listing associated with this application is provided in text format in lieu of a paper copy, and is hereby incorporated by reference into the specification. The name of the text file containing the Sequence Listing is Sequence_Listing_for_050760_54001US.txt. The text file is 4.00 KB, was created on Mar. 20, 2020, and is being submitted electronically via EFSWeb.

BACKGROUND OF THE INVENTION

Liraglutide (trade name Victoza), an analog of human GLP-1 and acted as a GLP-1 receptor agonist, is indicated as an adjunct to diet and exercise to improve glycemic control in adults with type 2 diabetes mellitus. Liraglutide includes a peptide having SEQ ID NO: 1, which has been engineered to be 97% homologous to native human GLP-1 by substituting arginine for lysine at position 34. Liraglutide is further derived from the noted engineered peptide by attaching a C-16 fatty acid (palmitic acid) through a glutamic acid spacer at the lysine residue of position 26. Accordingly, the structure of Liraglutide with noted modifications based on native human GLP-1 is shown below:

Liraglutide has a molecular formula of $C_{172}H_{265}N_{43}O_{51}$ and a molecular weight of 3751.2 Daltons. It was originally developed by Novo Nordisk, and approved by the U. S. Food and Drug Administration (FDA) on January 2010 under the trade name "Victoza".

U.S. Patent Publication No. 2015/0051372 A1 discloses a three-step method for purifying solid-phase synthetic crude liraglutide: sample treatment followed by three RP-HPLC purifications. In the sample treatment, crude liraglutide was dissolved in a mixture of acetonitrile and water (e.g., 20% acetonitrile/80% water by volume). The prepared sample was subjected to a first RP-HPLC purification, where mobile phase A (MPA) was 0.1% TFA/isopropanol/water; mobile phase B (MPB) was 0.1% TFA/acetonitrile; stationary phase was octylsilane bonded silica; and the gradient was a linear gradient. The fraction obtained by the first purification was then subjected to a second RP-HPLC purification, where MPA was 0.05-0.15% perchloric acid in water; MPB was 0.05-0.15% perchloric acid in acetonitrile; stationary phase was cyanosilane bonded silica; and the gradient was a linear gradient. The purified liraglutide was finally subjected to a third RP-HPLC purification for desalinization, where MPA was 0.05% aqueous ammonia solution; MPB was acetonitrile, stationary phase was octylsilane bonded silica; and the gradient was a linear gradient.

U.S. Pat. No. 9,422,330 B2 discloses a method for purifying crude liraglutide produced from yeast fermentation. As described in Example 6 of U.S. Pat. No. 9,422,330, the crude liraglutide was diluted with water and subjected to a RP-HPLC purification, where stationary phase was octadecyldimethylsilyl silica, which was initially equilibrated with a mobile phase of 20 mM Tris buffer/20% ethanol at pH 7.5. The column was first washed with the equilibration solution and eluted with a linear gradient followed by an isocratic gradient with a mobile phase including ethanol and 20 mM citrate buffer at pH 5.1. The target liraglutide was then eluted by a linear pH gradient elution from pH 5.1 to pH 4.0 with a mobile phase including ethanol and 20 mM citrate buffer. The chromatographic temperature was kept at 60° C.

Despite the above described purifying processes, there remains a need for the development of more efficient and improved processes for purifying liraglutide. The present disclosure addresses this need and provides related advantages as well.

BRIEF SUMMARY OF THE INVENTION

In a first aspect, the present invention provides a process for purifying liraglutide. The process includes:

(a) dissolving crude liraglutide in a solution comprising a halogenated solvent; and (b) subjecting the solution to a RP-HPLC purification system, and collecting purified liraglutide in fractions.

In a second aspect, the present application provides a process for purifying liraglutide. The process includes:

(a) dissolving crude liraglutide in a solution comprising a halogenated solvent; and (b) subjecting the solution to a RP-HPLC purification system, and collecting the purified liraglutide fractions, wherein the RP-HPLC purification system includes a first RP-HPLC purification and a second RP-HPLC purification; and (c) subjecting the fractions in step (b) to a third RP-HPLC purification using a mobile phase E including a sodium salt, water, and acetonitrile; and collecting fractions to obtain salt-exchanged liraglutide.

DETAILED DESCRIPTION OF THE INVENTION

I. General

Figure 1:
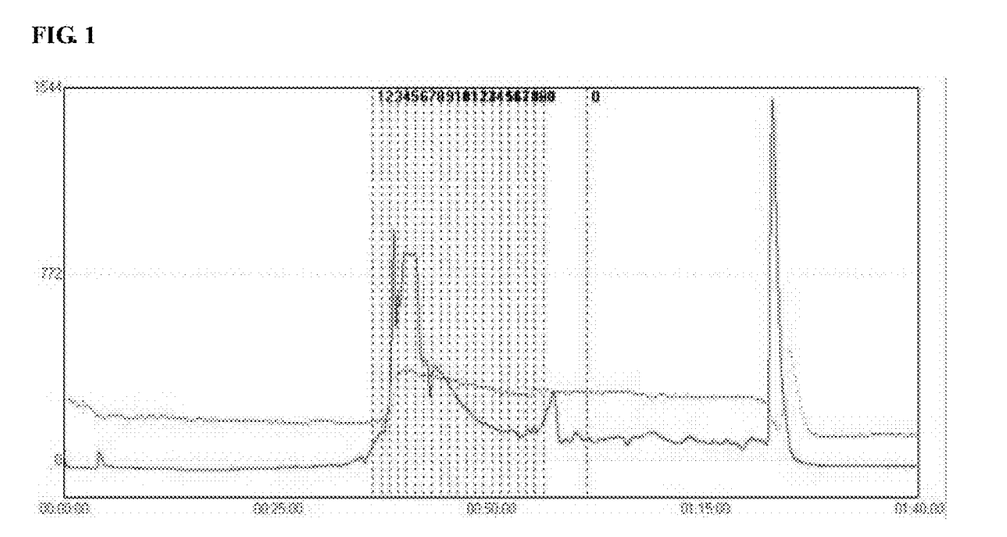
FIG. 1 shows elution chromatogram (full view) of the first purification according to Example 1.
Figure 2:
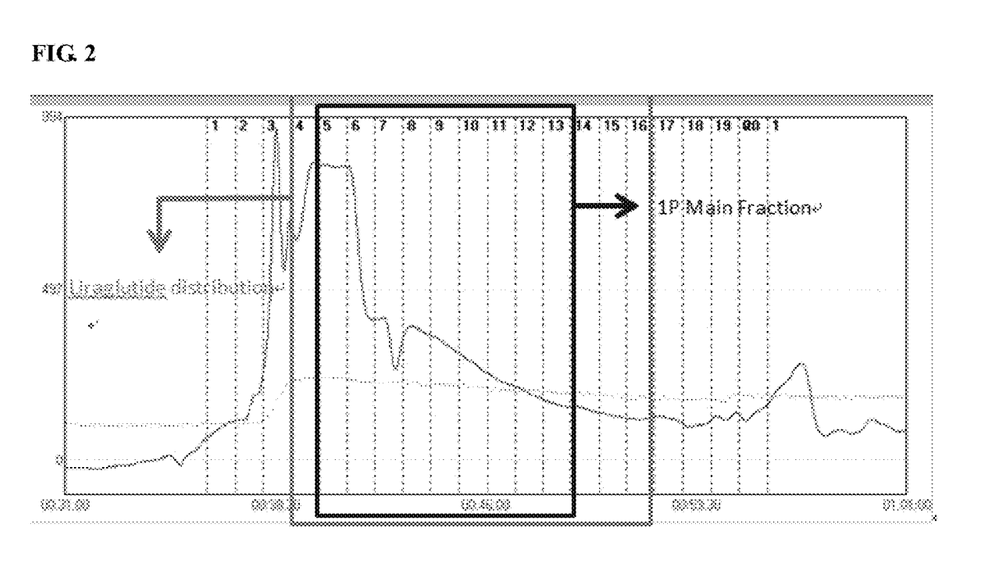
FIG. 2 shows elution chromatogram (zoom in) of FIG. 1. The fractions of from 5 to 13 as indicated were combined as 1P Main Fraction for the subsequent second purification.
Figure 3:
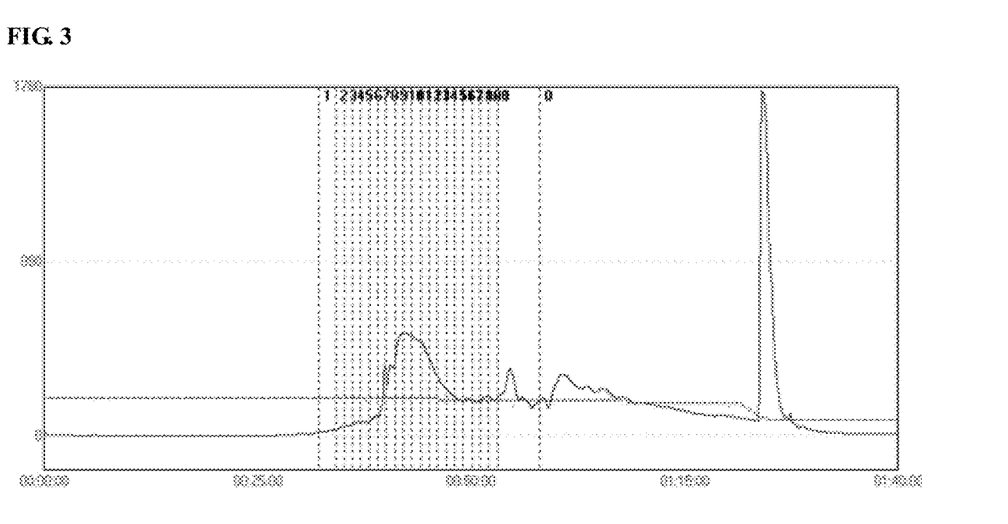
FIG. 3 shows elution chromatogram (full view) of the first purification according to Example 2 or 3.
Figure 4:
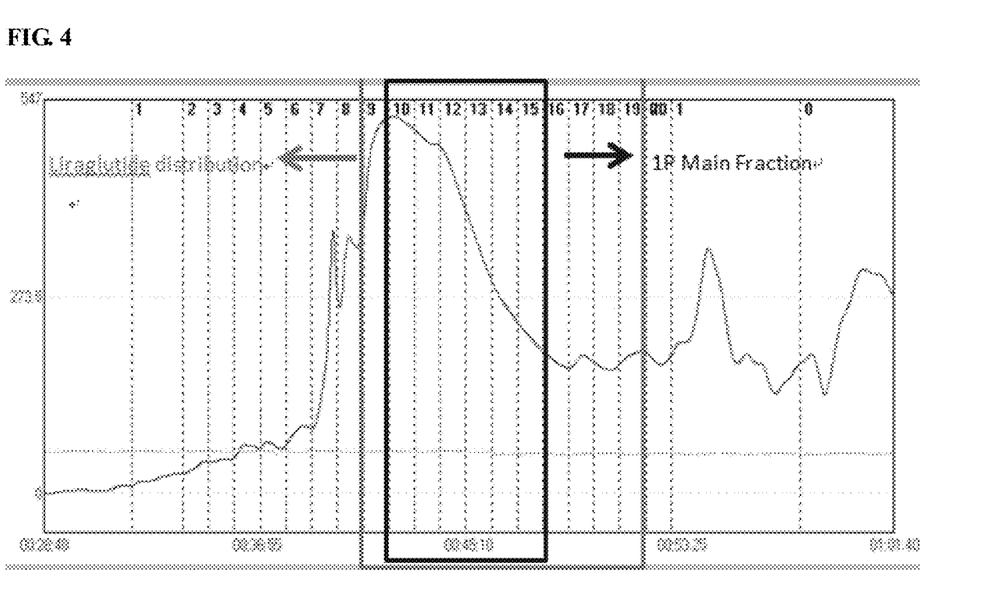
FIG. 4 shows elution chromatogram (zoom in) of FIG. 3. The fractions of from 10-15 as indicated were combined as 1P Main Fraction for the subsequent second purification.

The present invention provides improved processes for purifying liraglutide. Liraglutide is purified via two sequential RP-HPLC purifications followed by a salt-exchange step, where a pH is kept constant in the first and second purification steps. In particular, the processes utilize a halogenated solvent in a sample preparation step, which provides better solubility and an environment suitable for decarboxylation for crude liraglutide prior to a RP-HPLC purification. Tables A and B summarize advantages or characteristics of the present invention as compared to the processes disclosed in the art.

TABLES A

The Present Invention vs US2015/0051372

| Parameters | US2015/0051372 | Present Invention | Claimed Advantages |
|---|---|---|---|
| Solvent System for the Sample Preparation | a mixture of acetonitrile and water | a solution including a halogenated solvent (e.g., TFE, HFIP, TFA) | 1. Provide better solubility and decarboxylation condition for crude liraglutide; and 2. Prevent retention disturbing during the RP-HPLC purification |
| Stationary Phase | Two different stationary phase materials in three RP-HPLC purifications: First and third: octylsilane second: cyanosilane | Only one stationary phase material throughout three RP-HPLC purifications: octylsilane | Simple and convenient operations |

TFE: trifluoroethanol; HFIP: hexafluoroisopropanol; and TFA: trifluroacetic acid.

TABLES B

The Present Invention vs U.S. Pat. No. 9,422,330

| Parameters | U.S. Pat. No. 9,422,330 | Present Invention | Claimed Advantages |
|---|---|---|---|
| Gradient, pH | liraglutide is eluted with a pH gradient, which is close to the pI value of liraglutide | The pH is kept constant within each purification step (absence of a pH gradient) | 1. Elution of liraglutide beyond its pI value prevents the peptide from precipitation; and 2. Simple and convenient operations |

II. Definitions

SEQ ID NO: 1 refers to the amino acid sequence of the engineered peptide in Liraglutide. The sequence is represented by: H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-Gly-OH.

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

"RP-HPLC" refers to a reversed phase-high performance/pressure liquid chromatograph.

"Ammonium salt" refers to a class of chemical compounds which are composed of a cation of $NR_4^+$ and an anion, where R groups can be hydrogen or alkyl. In one embodiment, an ammonium salt refers to a class of chemical compounds which are composed of a cation of $NH_4^+$ and an anion. Ammonium salts useful in the present invention include ammonium formate and ammonium acetate.

"Phosphate salt" refers to a class of chemical compounds which are composed of a cation and a phosphate anion, such as the phosphate anion ($PO_4^{3-}$), the hydrogenphosphate anion ($HPO_4^{2-}$), and the dihydrogenphosphate anion ($H_2PO_4^-$). A phosphate salt having the anion of $PO_4^{3-}$ also refers to a phosphate tribasic salt; a phosphate salt having the anion of $HPO_4^{2-}$ also refers to a phosphate dibasic salt; and phosphate salt having the anion of $H_2PO_4^-$ also refers to a phosphate monobasic salt. Phosphate salts useful in the present invention include sodium phosphate tribasic ($Na_3PO_4$), sodium phosphate dibasic ($Na_2HPO_4$), sodium phosphate monobasic ($NaH_2PO_4$), potassium phosphate tribasic ($K_3PO_4$), potassium phosphate dibasic ($K_2HPO_4$), potassium phosphate monobasic ($KH_2PO_4$), ammonium phosphate tribasic (($NH_4)_3PO_4$), ammonium phosphate dibasic (($NH_4)_2HPO_4$), ammonium phosphate monobasic (($NH_4)H_2PO_4$).

III. Processes

In a first aspect, the present invention provides a process for purifying liraglutide. The process includes:

(a) dissolving crude liraglutide in a solution comprising a halogenated solvent; and (b) subjecting the solution to a RP-HPLC purification system, and collecting purified liraglutide in fractions.

In some embodiments, the halogenated solvent in step (a) is selected from the group consisting of fluorinated acid, fluorinated alcohol, chlorinated solvent, and mixtures thereof.

In some embodiments, the fluorinated alcohol is selected from the group consisting of 2,2,2-trifluoroethanol (TFE), 1,1,1,3,3,3-hexafluoro-2-propanol (HFIP), 2,2,3,3-tetrafluoro-1-propanol, 2,2,3,3,3-pentafluoro-1-propanol, pentafluorophenol, nonafluoro-tert-butyl alcohol, 3,3,4,4,4-pentafluoro-1-butanol, 4,4,5,5,5-pentafluoro-1-pentanol, 2,2,3,4,4,4-hexafluoro-1-butanol, 1,1,1,3,3,3-hexafluoro-2-methyl-2-propanol, 1,1,1,3,3,3-hexafluoro-2-phenyl-2-propanol, and mixtures thereof.

In some embodiments, the chlorinated solvent is 2,2,2-trichloroethanol.

In some embodiments, the fluorinated acid is trifluoroacetic acid.

In some embodiments, the solution in step (a) includes 5-35% fluorinated alcohol and 0.1-1% fluorinated acid by volume. In some embodiments, the solution in step (a) includes 15-20% 1,1,1,3,3,3-hexafluoro-2-propanol (HFIP) and 0.1-1% fluorinated acid by volume. In some embodiments, the solution in step (a) includes 20-30% 2,2,2-trifluoroethanol (TFE) and 0.1-1% fluorinated acid by volume. In some embodiments, the solution in step (a) includes 15-20% 1,1,1,3,3,3-hexafluoro-2-propanol (HFIP) and 0.1-1% trifluoroacetic acid by volume. In some embodiments, the solution in step (a) includes 20-30% 2,2,2-trifluoroethanol (TFE) and 0.1-1% trifluoroacetic acid by volume. In some embodiments, the solution in step (a) includes 15-20% 1,1,1,3,3,3-hexafluoro-2-propanol (HFIP) and 0.1-0.3% trifluoroacetic acid by volume. In some embodiments, the solution in step (a) includes 20-30% 2,2,2-trifluoroethanol (TFE) and 0.1-0.3% trifluoroacetic acid by volume. In some embodiments, the solution in step (a) includes about 17% 1,1,1,3,3,3-hexafluoro-2-propanol (HFIP) and about 0.2% trifluoroacetic acid by volume. In some embodiments, the solution in step (a) includes about 25% 2,2,2-trifluoroethanol (TFE) and about 0.2% trifluoroacetic acid by volume.

In some embodiments, the RP-HPLC purification system of step (b) includes a first RP-HPLC purification and a second RP-HPLC purification; the first RP-HPLC purification is conducted at a pH value of <7; and the second RP-HPLC purification is conducted at a pH value of >7.

In some embodiments, the first RP-HPLC purification is conducted at a pH value of <7; and the second RP-HPLC purification is conducted at a pH value of >about 7. In some embodiments, the first RP-HPLC purification is conducted at a pH value of <3; and the second RP-HPLC purification is conducted at a pH value of >about 7. In some embodiments, the first RP-HPLC purification is conducted at a pH value of <3; and the second RP-HPLC purification is conducted at a pH value of >about 7.5.

In some embodiments, the first RP-HPLC purification uses a mobile phase A including trifluoroacetic acid and water and a mobile phase B including trifluoroacetic acid and acetonitrile.

In some embodiments, the mobile phase A and mobile phase B include each 0.1-1% trifluoroacetic acid by volume. In some embodiments, the mobile phase A and mobile phase B include each 0.1-0.5% trifluoroacetic acid by volume. In some embodiments, the mobile phase A and mobile phase B include each 0.1-0.3% trifluoroacetic acid by volume. In some embodiments, the mobile phase A and mobile phase B include each about 0.2% trifluoroacetic acid by volume. In some embodiments, the mobile phase A is a solution of 0.2% trifluoroacetic acid in water; and mobile phase B is a solution of about 0.2% trifluoroacetic acid in acetonitrile.

In some embodiments, the mobile phase B is eluted at a linear gradient of from 5-25% to 80-100% by volume. In some embodiments, the mobile phase B is eluted at a linear gradient of from 5-15% to 90-100% by volume. In some embodiments, the mobile phase B is eluted at a linear gradient of from 5-25% to 80-100% by volume, wherein the mobile phase A is a solution of 0.2% trifluoroacetic acid in water; and mobile phase B is a solution of about 0.2% trifluoroacetic acid in acetonitrile. In some embodiments, the mobile phase B is eluted at a linear gradient of from 5-15% to 90-100% by volume, wherein the mobile phase A is a solution of 0.2% trifluoroacetic acid in water; and mobile phase B is a solution of about 0.2% trifluoroacetic acid in acetonitrile. In some embodiments, the mobile phase B is eluted at a linear gradient of from about 10% to 95% by volume, wherein the mobile phase A is a solution of 0.2% trifluoroacetic acid in water; and mobile phase B is a solution of about 0.2% trifluoroacetic acid in acetonitrile. In some embodiments, the mobile phase B is eluted at a linear gradient of from about 10% to 95% by volume according to the gradient of Table 1, wherein the mobile phase A is a solution of 0.2% trifluoroacetic acid in water; and mobile phase B is a solution of about 0.2% trifluoroacetic acid in acetonitrile.

In some embodiments, the second RP-HPLC purification uses a mobile phase C including an ammonium salt or a phosphate salt and a mobile phase D including acetonitrile. In some embodiments, the second RP-HPLC purification uses a mobile phase C including an ammonium salt and a mobile phase D including acetonitrile. In some embodiments, the second RP-HPLC purification uses a mobile phase C including a phosphate salt and a mobile phase D including acetonitrile. In some embodiments, the second RP-HPLC purification uses a mobile phase C and a mobile phase D, each of which includes an ammonium salt or a phosphate salt. In some embodiments, the second RP-HPLC purification uses a mobile phase C and a mobile phase D, each of which includes an ammonium salt. In some embodiments, the second RP-HPLC purification uses a mobile phase C including an aqueous solution of an ammonium salt and a mobile phase D including an aqueous solution of an ammonium salt and acetonitrile. In some embodiments, the second RP-HPLC purification uses a mobile phase C including an aqueous solution of a phosphate salt and a mobile phase D being acetonitrile.

In some embodiments, the mobile phase C further includes acetonitrile in an amount of from 1% to 10% by volume. In some embodiments, the mobile phase C further includes acetonitrile in an amount of from 3% to 7% by volume. In some embodiments, the mobile phase C further includes acetonitrile in an amount of about 5% by volume.

In some embodiments, the mobile phase D further includes an aqueous solution of an ammonium salt in an amount of from 10% to 60% by volume. In some embodiments, the mobile phase D further includes an aqueous solution of an ammonium salt in an amount of from 20% to 60%, 30% to 60%, 4% to 60%, or about 50% by volume. In some embodiments, the mobile phase D further includes an aqueous solution of an ammonium salt in an amount of about 50% by volume.

In some embodiments, the ammonium salt is selected from the group consisting of ammonium formate, ammonium acetate, and mixtures thereof. In some embodiments, the ammonium salt is ammonium formate.

In some embodiments, the phosphate salt is selected from the group consisting of sodium phosphate tribasic, sodium phosphate dibasic, sodium phosphate monobasic, potassium phosphate tribasic, potassium phosphate dibasic, potassium phosphate monobasic, ammonium phosphate tribasic, ammonium phosphate dibasic, ammonium phosphate monobasic, and mixtures thereof. In some embodiments, the phosphate salt is selected from the group consisting of sodium phosphate dibasic, sodium phosphate monobasic, potassium phosphate dibasic, potassium phosphate monobasic, ammonium phosphate dibasic, ammonium phosphate monobasic, and mixtures thereof. In some embodiments, the phosphate salt is selected from the group consisting of potassium phosphate dibasic, potassium phosphate monobasic, and mixtures thereof. In some embodiments, the phosphate salt is a mixture of potassium phosphate dibasic and potassium phosphate monobasic.

In some embodiments, the mobile phase C includes the ammonium salt or phosphate salt in a concentration of from 5 to 50 mM in water. In some embodiments, the mobile phase C includes the ammonium salt or phosphate salt in a concentration of from 10 to 40 mM in water. In some embodiments, the mobile phase C includes the ammonium salt or phosphate salt in a concentration of from 10 to 30 mM, from 15 to 25 mM, or about 20 mM in water. In some embodiments, the mobile phase C includes the ammonium salt or phosphate salt in a concentration of about 20 mM in water. In some embodiments, the mobile phase C includes the ammonium salt in a concentration of about 20 mM in water. In some embodiments, the mobile phase C includes an aqueous solution of 20 mM ammonium salt. In some embodiments, the mobile phase C includes the phosphate salt in a concentration of about 20 mM in water. In some embodiments, the mobile phase C includes an aqueous solution of 20 mM phosphate salt.

In some embodiments, the mobile phase C has a pH value of from about 7.5 to about 9.0 or from about 7.5 to about 8.5. In some embodiments, the mobile phase C has a pH value of from about 7.5 to about 8.5. In some embodiments, the mobile phase C has a pH value of about 8.5. In some embodiments, the mobile phase C has a pH value of about 7.9.

In some embodiments, mobile phase C includes an aqueous solution of ammonium formate. In some embodiments, mobile phase C includes an aqueous solution of 20 mM ammonium formate. In some embodiments, mobile phase C includes an aqueous solution of 20 mM ammonium formate; and has a pH value of about 8.5. In some embodiments, mobile phase C includes acetonitrile and an aqueous solution of 20 mM ammonium formate; and has a pH value of about 8.5, wherein the aqueous solution and acetonitrile has a ratio of 95 to 5 by volume.

In some embodiments, mobile phase C includes an aqueous solution of potassium phosphate dibasic and potassium phosphate monobasic. In some embodiments, mobile phase C includes an aqueous solution of potassium phosphate dibasic and potassium phosphate monobasic in a concentration of 20 mM. In some embodiments, mobile phase C includes an aqueous solution of potassium phosphate dibasic and potassium phosphate monobasic in a concentration of 20 mM; and has a pH value of about 7.9. In some embodiments, mobile phase C includes acetonitrile and an aqueous solution of potassium phosphate dibasic and potassium phosphate monobasic in a concentration of 20 mM; and has a pH value of about 7.9, wherein potassium phosphate dibasic and potassium phosphate monobasic has a ratio of 12 to 1 by weight, and the aqueous solution and acetonitrile has a ratio of 95 to 5 by volume.

In some embodiments, the mobile phase D has a pH value of from about 7.5 to about 9.0 or from about 7.5 to about 8.5. In some embodiments, the mobile phase D has a pH value of from about 7.5 to about 8.5. In some embodiments, the mobile phase D has a pH value of about 8.5.

In some embodiments, mobile phase D further includes an aqueous solution of ammonium formate. In some embodiments, mobile phase D further includes an aqueous solution of 20 mM ammonium formate. In some embodiments, mobile phase D further includes an aqueous solution of 20 mM ammonium formate; and has a pH value of about 8.5. In some embodiments, mobile phase D includes an aqueous solution of 20 mM ammonium formate and acetonitrile; and has a pH value of about 8.5, wherein the aqueous solution and acetonitrile has a ratio of 50 to 50 by volume.

In some embodiments, mobile phase D is acetonitrile.

In some embodiments, mobile phase C includes an aqueous solution of 20 mM ammonium formate and acetonitrile and has a pH value of about 8.5; and mobile phase D includes an aqueous solution of 20 mM ammonium formate and acetonitrile and has a pH value of about 8.5, wherein the aqueous solution and acetonitrile in the mobile phase C has a ratio of 95 to 5 by volume and the aqueous solution and acetonitrile in the mobile phase D has a ratio of 50 to 50 by volume.

In some embodiments, mobile phase C includes acetonitrile and an aqueous solution of potassium phosphate dibasic and potassium phosphate monobasic in a concentration of 20 mM and has a pH value of about 7.9; and mobile phase D is acetonitrile, wherein potassium phosphate dibasic and potassium phosphate monobasic has a ratio of 12 to 1 by weight, and the aqueous solution and acetonitrile in the mobile phase C has a ratio of 95 to 5 by volume.

In some embodiments, the mobile phase D is eluted at linear gradient from 0-10% to 50-100% by volume. In some embodiments, the mobile phase D is eluted at linear gradient from 0% to 100% by volume, wherein mobile phase C includes an aqueous solution of 20 mM ammonium formate and acetonitrile and has a pH value of about 8.5; and mobile phase D includes an aqueous solution of 20 mM ammonium formate and acetonitrile and has a pH value of about 8.5, wherein the aqueous solution and acetonitrile in the mobile phase C has a ratio of 95 to 5 by volume and the aqueous solution and acetonitrile in the mobile phase D has a ratio of 50 to 50 by volume. In some embodiments, the mobile phase D is eluted at linear gradient from 0% to 100% by volume according to the gradient of Table 2, wherein mobile phase C includes an aqueous solution of 20 mM ammonium formate and acetonitrile and has a pH value of about 8.5; and mobile phase D includes an aqueous solution of 20 mM ammonium formate and acetonitrile and has a pH value of about 8.5, wherein the aqueous solution and acetonitrile in the mobile phase C has a ratio of 95 to 5 by volume and the aqueous solution and acetonitrile in the mobile phase D has a ratio of 50 to 50 by volume. In some embodiments, the mobile phase D is eluted at linear gradient from 5% to 70% by volume, wherein mobile phase C includes acetonitrile and an aqueous solution of potassium phosphate dibasic and potassium phosphate monobasic in a concentration of 20 mM and has a pH value of about 7.9; and mobile phase D is acetonitrile, wherein potassium phosphate dibasic and potassium phosphate monobasic has a ratio of 12 to 1 by weight, and the aqueous solution and acetonitrile in the mobile phase C has a ratio of 95 to 5 by volume. In some embodiments, the mobile phase D is eluted at linear gradient from 5% to 70% by volume according to the gradient Table 3, wherein mobile phase C includes acetonitrile and an aqueous solution of potassium phosphate dibasic and potassium phosphate monobasic in a concentration of 20 mM and has a pH value of about 7.9; and mobile phase D is acetonitrile, wherein potassium phosphate dibasic and potassium phosphate monobasic has a ratio of 12 to 1 by weight, and the aqueous solution and acetonitrile in the mobile phase C has a ratio of 95 to 5 by volume.

In some embodiments, the purified liraglutide in fractions has a pH value of from about 7.5 to about 8.5. In some embodiments, the purified liraglutide in fractions has a pH value of from about 8.0 to about 8.5. In some embodiments, the purified liraglutide in fractions has a pH value of from about 7.5 to about 8.0.

The flow rate of the first and second purification depends on the size of the RP-HPLC preparation column. In some embodiments, the flow rate of the first purification is from about 50 to 200 mL/min, when the column has a diameter and length of from 5 cm×22 cm to 8 cm×12.6 cm. In some embodiments, the flow rate of the first purification is from about 100 to 160 mL/min, when the column has a diameter and length of from 5 cm×22 cm to 8 cm×12.6 cm. In some embodiments, the flow rate of the first purification is about 104 mL/min, when the column has a diameter and length of 5 cm×22 cm. In some embodiments, the flow rate of the first purification is about 152 mL/min, when the column has a diameter and length of 8 cm×12.6 cm. In some embodiments, the flow rate of the first purification is from 4 to 8 mL/min, when the column has a diameter and length of 10 mm×250 mm. In some embodiments, the flow rate of the first purification is about 4.7 mL/min, when the column has a diameter and length of 10 mm×250 mm. In some embodiments, the flow rate of the second purification is from about 50 to 200 mL/min, when the column has a diameter and length of from 5 cm×22 cm to 8 cm×12.6 cm. In some embodiments, the flow rate of the second purification is from about 100 to 160 mL/min, when the column has a diameter and length of from 5 cm×22 cm to 8 cm×12.6 cm. In some embodiments, the flow rate of the second purification is about 152 mL/min, when the column has a diameter and length of 8 cm×12.6 cm. In some embodiments, the flow rate of the second purification is from about 0.3 to 0.5 mL/min, when the column has a diameter and length of 4.6 mm×100 mm. In some embodiments, the flow rate of the second purification is about 0.4 mL/min, when the column has a diameter and length of 4.6 mm×100 mm.

In some embodiments, the crude liraglutide of step (a) is obtained from solid-phase synthesis.

In some embodiments, further comprising:
(c) subjecting the fractions in step (b) to a third RP-HPLC purification using a mobile phase E comprising a sodium salt, water, and acetonitrile; and collecting fractions to obtain salt-exchanged liraglutide.

In some embodiments, the sodium salt is sodium phosphate dibasic.

In some embodiments, the mobile phase E includes an aqueous solution of sodium phosphate dibasic. In some embodiments, mobile phase E includes an aqueous solution of sodium phosphate dibasic in a concentration of 20 mM. In some embodiments, mobile phase E includes an aqueous solution of sodium phosphate dibasic in a concentration of 20 mM; and has a pH value of about 8.0. In some embodiments, mobile phase E (as E1) includes acetonitrile and an aqueous solution of sodium phosphate dibasic in a concentration of 20 mM; and has a pH value of about 8.0, wherein the aqueous solution and acetonitrile has a ratio of 95 to 5 by volume. In some embodiments, mobile phase E (as E2) includes acetonitrile and an aqueous solution of sodium phosphate dibasic in a concentration of 20 mM; and has a pH value of about 8.0, wherein the aqueous solution and acetonitrile has a ratio of 50 to 50 by volume.

In some embodiments, step (c) is conducted by applying the mobile phase E1 followed by the mobile phase E2, thereby providing a salt-exchanged liraglutide in fractions.

The flow rate of the third purification depends on the size of the RP-HPLC preparation column. In some embodiments, the flow rate of the third purification is from 4 to 8 mL/min, when the column has a diameter and length of 10 mm×250 mm. In some embodiments, the flow rate of the first purification is about 4.7 mL/min, when the column has a diameter and length of 10 mm×25 cm.

In some embodiments, the salt-exchanged liraglutide in fractions has a pH value of from about 7.5 to about 8.0.

In some embodiments, the first, second, and third RP-HPLC purifications have the same stationary phase.

In a second aspect, the present application provides a process for purifying liraglutide. The process includes:
(a) dissolving crude liraglutide in a solution comprising a halogenated solvent; and
(b) subjecting the solution to a RP-HPLC purification system, and collecting the purified liraglutide fractions, wherein the RP-HPLC purification system includes a first RP-HPLC purification and a second RP-HPLC purification; and
(c) subjecting the fractions in step (b) to a third RP-HPLC purification using a mobile phase E including a sodium salt, water, and acetonitrile; and collecting fractions to obtain salt-exchanged liraglutide.

Suitable conditions for steps a) to (c) for the second aspect are the same as ones as defined and described in the first aspect.

IV. Examples

The following examples are provided to further illustrate, but not to limit this invention.

Example 1

Sample Pretreatment:
The crude liraglutide was obtained from solid-phase synthesis with a purity of 44.6%. 30 g crude liraglutide was dissolved in 500 mL triflouroethanol (TFE) solution (25% TFE in 0.2% trifluoroacetic acid). The mixture was then stirred at room temperature (RT) for about 2 hrs.

First Purification:
The obtained solution was loaded onto a RP-HPLC preparative column packed with C8, 10 μm silica having a diameter and length of 8 cm×12.6 cm. The loading amount was 27.1 g.

A purification cycle was performed with condition of:
(1) mobile phase A: 0.2% trifluoroacetic acid (TFA) in water;
(2) mobile phase B: 0.2% TFA in acetonitrile (ACN);
(3) flow rate: 152 mL/min; and
(4) elution gradient Table 1:

| Time | Composition | |
| --- | --- | --- |
| (minute:second) | MPA (%) by volume | MPB (%) by volume |
| 00:00 | 90 | 10 |
| 10:00 | 90 | 10 |

-continued

| Time | Composition | |
|---|---|---|
| (minute:second) | MPA (%) by volume | MPB (%) by volume |
| 40:00 | 60 | 40 |
| 80:00 | 45 | 55 |
| 80:06 | 5 | 95 |
| 100:06 | 5 | 95 |

Fractions containing liraglutide with 90.58% purity were obtained and transferred to second purification.

Second Purification:

Fractions containing liraglutide with 90.58% purity were adjusted with 33% Ammonium to pH value of 8.5 and diluted with 20 mM ammonium formate with pH value of 8.5, and then loaded onto RP-HPLC column packed with C8, 10 μm silica having a diameter and length of 8 cm×12.6 cm. The loading amount was 6.2 g.

A purification cycle was performed with condition of:
(1) mobile phase C: 20 mM ammonium formate (AmF) adjusted to pH value of 8.5 and diluted with ACN to the ratio of 95/5 (V/V);
(2) mobile phase D: 20 mM AmF adjusted to pH value of 8.5 and diluted with ACN to the ratio of 50/50 (V/V);
(3) flow rate: 152 mL/min; and
(4) elution gradient Table 2:

| Time | Composition | |
|---|---|---|
| (minute:second) | MPC (%) by volume | MPD (%) by volume |
| 00:00 | 100 | 0 |
| 05:00 | 100 | 0 |
| 15:00 | 45 | 55 |
| 65:00 | 23 | 77 |
| 75:00 | 0 | 100 |
| 120:00 | 0 | 100 |

Fractions containing liraglutide with 98.48% purity and pH value about 8.0-8.5 were obtained and transferred to third purification (salt exchange).

Third Purification (Salt Exchange):

Fractions containing liraglutide with 98.48% purity were loaded onto RP-HPLC column packed with C8, 10 μm silica having a diameter and length of 10 mm×250 mm with a flow rate of 4.7 mL/min. The loading amount was 1.1 g. After loaded, the column was flushed with 20 mM sodium phosphate dibasic solution (pH=8.0) comprising 5% acetonitrile, and then eluted with 20 mM sodium phosphate dibasic solution (pH=8.0) comprising 50% acetonitrile. Thus, salt-exchanged liraglutide with pH value about 7.5-8.0 was obtained, and then lyophilized, resulting in 3.3 g liraglutide concentrate with 98.48% purity.

Example 2

Sample Pretreatment:

The crude liraglutide was obtained from solid-phase synthesis with a purity of 33.8%. 19.5 gram crude liraglutide was dissolved in 238 mL hexafluoroisopropanol (HFIP) solution (17% HFIP in 0.2% TFA solution). The mixture was then stirred at room temperature (RT) for about 2 hrs.

First Purification:

The obtained solution was loaded onto a RP-HPLC preparative column packed with C8, 10 μm silica having a diameter and length of 5 cm×22 cm. The loading amount was 19.5 g.

A purification cycle was performed with condition of:
(1) mobile phase A: 0.2% trifluoroacetic acid (TFA) in water;
(2) mobile phase B: 0.2% TFA in acetonitrile (ACN);
(3) flow rate: 104 mL/min; and
(4) elution gradient Table 1:

| Time | Composition | |
|---|---|---|
| (minute:second) | MPA (%) by volume | MPB (%) by volume |
| 00:00 | 90 | 10 |
| 10:00 | 90 | 10 |
| 40:00 | 60 | 40 |
| 80:00 | 45 | 55 |
| 80:06 | 5 | 95 |
| 100:06 | 5 | 95 |

Fractions containing liraglutide with 89.65% purity were obtained and transferred to second purification. The loading amount was 4.3 g.

Second Purification and Third Purification (Salt Exchange):

Fractions containing liraglutide with 89.65% purity were then subjected to second purification and third purification (salt exchange) that have the same purifying condition and method with the Example 1. Thus, salt-exchanged liraglutide with pH value about 7.5-8.0 was obtained, and then lyophilized, resulting in 3.7 g liraglutide concentrate with 97.23% purity.

Example 3

Sample Pretreatment:

The crude liraglutide was obtained from solid-phase synthesis with a purity of 33.8%. 990.3 milligram crude liraglutide was dissolved in 11.22 mL hexafluoroisopropanol (HFIP) solution (17% HFIP in 0.2% TFA solution). The mixture was then stirred at room temperature (RT) for about 2 hrs.

First Purification:

The obtained solution was loaded onto a RP-HPLC preparative column packed with C8, 10 μm silica having a diameter and length of 10 mm×25 cm. The loading amount was 0.99 g.

A purification cycle was performed with condition of:
(1) mobile phase A: 0.2% trifluoroacetic acid (TFA) in water;
(2) mobile phase B: 0.2% TFA in acetonitrile (ACN);
(3) flow rate: 4.7 mL/min; and
(4) elution gradient Table 1:

| Time | Composition | |
|---|---|---|
| (minute:second) | MPA (%) by volume | MPB (%) by volume |
| 00:00 | 90 | 10 |
| 10:00 | 90 | 10 |
| 40:00 | 60 | 40 |
| 80:00 | 45 | 55 |
| 80:06 | 5 | 95 |
| 100:06 | 5 | 95 |

Fractions containing liraglutide with 92.17% purity were obtained and transferred to second purification. The loading amount was 41.1 milligram.

Second Purification:

Fractions containing liraglutide with 92.17% purity were diluted with mobile phase C, and then loaded onto RP-HPLC column packed with C8, 10 μm silica having a diameter and length of 4.6 mm×100 mm.

A purification cycle was performed with condition of:
(1) mobile phase C: 20 mM potassium phosphate dibasic ($K_2HPO_4$)/potassium phosphate monobasic ($KH_2PO_4$)=12/1, adjusted to pH value of 7.9, and diluted with ACN to the ratio of 95/5 (V/V);
(2) mobile phase D: ACN;
(3) flow rate: 0.4 mL/min; and
(3) elution gradient Table 3:

| Time (minute:second) | Composition | |
|---|---|---|
| | MPC (%) by volume | MPD (%) by volume |
| 00:00 | 95 | 5 |
| 10:00 | 95 | 5 |
| 23:00 | 80 | 20 |
| 98:00 | 55 | 45 |
| 98:06 | 30 | 70 |
| 118:06 | 30 | 70 |

Fractions containing liraglutide with 97% purity and pH value about 7.5-8.0 were obtained and transferred to third purification (salt exchange).

Third Purification (Salt Exchange):

Third purification (salt exchange) has the same purifying condition and method with the Example 1. Thus, salt-exchanged liraglutide with pH value about 7.5-8.0 was obtained, and then lyophilized.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for purifying liraglutide, comprising:
(a) dissolving crude liraglutide in a solution comprising a halogenated solvent; and
(b) subjecting the solution to a RP-HPLC purification system, and collecting purified liraglutide in fractions.

2. The process according to claim 1, wherein the halogenated solvent in step (a) is selected from the group consisting of a fluorinated acid, a fluorinated alcohol, a chlorinated solvent, and mixtures thereof.

3. The process according to claim 2, wherein the fluorinated alcohol is selected from the group consisting of 2,2,2-trifluoroethanol (TFE), 1,1,1,3,3,3-hexafluoro-2-propanol (HFIP), 2,2,3,3-tetrafluoro-1-propanol, 2,2,3,3,3-pentafluoro-1-propanol, pentafluorophenol, nonafluoro-tert-butyl alcohol, 3,3,4,4,4-pentafluoro-1-butanol, 4,4,5,5,5-pentafluoro-1-pentanol, 2,2,3,4,4,4-hexafluoro-1-butanol, 1,1,1,3,3,3-hexafluoro-2-methyl-2-propanol, 1,1,1,3,3,3-hexafluoro-2-phenyl-2-propanol, and mixtures thereof.

4. The process according to claim 2, wherein the chlorinated solvent is 2,2,2-trichloroethanol.

5. The process according to claim 2, wherein the fluorinated acid is trifluoroacetic acid.

6. The process according to claim 2, wherein the solution in step (a) comprises 5-35% fluorinated alcohol and 0.1-1% fluorinated acid by volume.

7. The process according to claim 6, wherein the solution in step (a) comprises 15-20% 1,1,1,3,3,3-hexafluoro-2-propanol (HFIP) and 0.1-1% fluorinated acid by volume.

8. The process according to claim 6, wherein the solution in step (a) comprises 20-30% 2,2,2-trifluoroethanol (TFE) and 0.1-1% fluorinated acid by volume.

9. The process according to claim 1, wherein the RP-HPLC purification system of step (b) comprises a first RP-HPLC purification and a second RP-HPLC purification; the first RP-HPLC purification is conducted at a pH value of <7; and the second RP-HPLC purification is conducted at a pH value of >7.

10. The process according to claim 9, wherein the first RP-HPLC purification is conducted at a pH value of <3; and the second RP-HPLC purification is conducted at a pH value of >about 7.5.

11. The process according to claim 9, wherein the first RP-HPLC purification uses a mobile phase A comprising trifluoroacetic acid and water and a mobile phase B comprising trifluoroacetic acid and acetonitrile.

12. The process according to claim 11, wherein the mobile phase A and mobile phase B comprise each 0.1-1% trifluoroacetic acid by volume.

13. The process according to claim 12, wherein the mobile phase B is eluted at a linear gradient of from 5-25% to 80-100% by volume.

14. The process according to claim 9, wherein the second RP-HPLC purification uses a mobile phase C comprising an ammonium salt or a phosphate salt and a mobile phase D comprising acetonitrile.

15. The process according to claim 14, wherein the ammonium salt is selected from the group consisting of ammonium formate, ammonium acetate, and mixtures thereof.

16. The process according to claim 14, wherein the phosphate salt is selected from the group consisting of sodium phosphate tribasic, sodium phosphate dibasic, sodium phosphate monobasic, potassium phosphate tribasic, potassium phosphate dibasic, potassium phosphate monobasic, ammonium phosphate tribasic, ammonium phosphate dibasic, ammonium phosphate monobasic, and mixtures thereof.

17. The process according to claim 14, wherein the mobile phase C comprises the ammonium salt or phosphate salt in a concentration of from 5 to 50 mM in water.

18. The process according to claim 14, wherein the mobile phase C has a pH value of from about 7.5 to about 9.0 or from about 7.5 to about 8.5.

19. The process according to claim 14, wherein the mobile phase D is eluted at linear gradient from 0-10% to 50-100% by volume.

20. The process according to claim 14, wherein the purified liraglutide in fractions has a pH value of from about 7.5 to about 8.5.

21. The process according to claim 1, further comprising:
(c) subjecting the fractions in step (b) to a third RP-HPLC purification using a mobile phase E comprising a sodium salt, water, and acetonitrile; and collecting fractions to obtain salt-exchanged liraglutide.

22. The process according to claim 21, wherein the sodium salt is sodium phosphate dibasic.

23. The process according to claim 21, wherein the salt-exchanged liraglutide in fractions has a pH value of from about 7.5 to about 8.0.

* * * * *